(12) United States Patent
Nock

(10) Patent No.: US 12,721,609 B2
(45) Date of Patent: Sep. 1, 2026

(54) SHAPE MEMORY MARKER DEPLOYMENT DEVICE

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 729 days.

(21) Appl. No.: 17/527,296

(22) Filed: Nov. 16, 2021

(65) Prior Publication Data

US 2022/0071608 A1 Mar. 10, 2022

Related U.S. Application Data

(63) Continuation of application No. PCT/US2020/035056, filed on May 29, 2020.

(Continued)

(51) Int. Cl.
*A61B 10/02* (2006.01)
*A61B 90/00* (2016.01)

(52) U.S. Cl.
CPC .......... *A61B 10/0275* (2013.01); *A61B 90/39* (2016.02); *A61B 2090/3908* (2016.02); *A61B 2090/3987* (2016.02)

(58) Field of Classification Search
CPC ................ A61B 10/0275; A61B 90/39; A61B 2090/3908; A61B 2090/3987
See application file for complete search history.

(56) References Cited

U.S. PATENT DOCUMENTS 4,984,581 A * 1/1991 Stice .................... A61M 25/09 604/95.01
5,902,310 A * 5/1999 Foerster ................ A61B 90/39 606/151

(Continued)

FOREIGN PATENT DOCUMENTS

CN 109009344 A * 12/2018 ............ A61B 17/34
DE 202004017888 U1 5/2005

(Continued)

OTHER PUBLICATIONS

CN109009344A English Translation (Year: 2018).*
International Search Report and Written Opinion dated Sep. 4, 2020 for Application No. PCT/US20/35056, 13 pages.

*Primary Examiner* — Aurelie H Tu
*Assistant Examiner* — Andrew E Hoffpauir
(74) *Attorney, Agent, or Firm* — FBT Gibbons LLP

(57) ABSTRACT

A marker delivery device includes an outer cannula, an inner cannula assembly, and a push rod. The outer cannula defines a longitudinal axis and includes an outer lumen. The outer lumen extends distally along the longitudinal axis from a handle to an open outer cannula distal end. The inner cannula assembly includes an inner cannula and a grip. The inner cannula is disposed within the outer lumen and extends distally along the longitudinal axis from the grip to an open distal end. The inner cannula has a resilient portion located proximate the open distal end. The resilient portion is configured to move between a stressed configuration when engaged with the outer cannula and a relaxed configuration when disengaged with the outer cannula. The push rod is disposed within an inner lumen of the inner cannula and is configured to deploy a marker through the open distal end.

20 Claims, 16 Drawing Sheets

Related U.S. Application Data

(60) Provisional application No. 62/854,561, filed on May 30, 2019.

(56) References Cited

U.S. PATENT DOCUMENTS 6,083,524 A 7/2000 Sawhney et al.
6,162,241 A 12/2000 Coury et al.
6,261,302 B1 * 7/2001 Voegele ................ A61B 90/39 606/151
6,270,464 B1 8/2001 Fulton, III et al.
6,356,782 B1 3/2002 Sirimanne et al.
6,605,294 B2 8/2003 Sawhney
8,079,964 B2 * 12/2011 Reichel ................ A61B 90/39 600/593
8,529,465 B2 9/2013 Speeg et al.
8,600,481 B2 12/2013 Sirimanne et al.
8,939,910 B2 1/2015 Fisher
2003/0199760 A1 * 10/2003 Curpen ................ A61B 90/39 600/434
2006/0167416 A1 * 7/2006 Mathis .............. A61B 18/1477 604/164.01
2008/0015540 A1 * 1/2008 Muni ................ A61B 17/3421 604/502
2009/0177272 A1 * 7/2009 Abbate ................ A61L 31/148 623/1.42
2009/0192408 A1 * 7/2009 Mark .................... A61B 90/39 600/562
2009/0196470 A1 * 8/2009 Carl ......................... G06T 7/33 382/128
2011/0218433 A1 * 9/2011 Speeg ................... A61B 10/02 600/432
2012/0046664 A1 * 2/2012 McGuckin, Jr. .. A61M 25/0041 606/93
2013/0041256 A1 * 2/2013 Fiebig ............... A61B 17/3468 600/432
2014/0046334 A1 * 2/2014 Schaus .............. A61B 17/8822 606/93
2016/0278809 A1 * 9/2016 Sato ........................ A61B 1/06
2017/0231716 A1 * 8/2017 Ahari .................... A61B 10/02 600/431
2018/0140288 A1 * 5/2018 Householder ...... A61B 10/0275
2021/0030404 A1 * 2/2021 Van Liere .......... A61B 17/3403
2022/0192722 A1 * 6/2022 Harshman .......... A61B 17/3472

FOREIGN PATENT DOCUMENTS

EP 2092906 A2 8/2009
WO 2010/077244 A1 7/2010

* cited by examiner

SHAPE MEMORY MARKER DEPLOYMENT DEVICE

PRIORITY

This application is a continuation of International Application Number PCT/US2020/035056 entitled "Shape Memory Marker Deployment Device," filed on May 29, 2020, which claims priority to U.S. Provisional Application Ser. No. 62/854,561 entitled "Shape Memory Marker Deployment Device," filed on May 30, 2019, the disclosures of which are incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

Markers are used after breast biopsies to mark the location where the biopsied tissue was removed. Various markers are described in the following US Patents: U.S. Pat. No. 6,083,524, "Polymerizable Biodegradable Polymers Including Carbonate or Dioxanone Linkages," issued Jul. 4, 2000; U.S. Pat. No. 6,162,241, "Hemostatic Tissue Sealants," issued Dec. 4, 2000; U.S. Pat. No. 6,270,464, "Biopsy Localization Method and Device," issued Aug. 7, 2001; U.S. Pat. No. 6,356,782, "Subcutaneous Cavity Marking Device and Method," issued Mar. 12, 2002; U.S. Pat. No. 6,605,294, "Methods of Using In Situ Hydration of Hydrogel Articles for Sealing or Augmentation of Tissue or Vessels," issued Aug. 12, 2003; U.S. Pat. No. 8,600,481, "Subcutaneous Cavity Marking Device," issued Dec. 3, 2013 and U.S. Pat. No. 8,939,910, "Method for Enhancing Ultrasound Visibility of Hyperechoic Materials", issued Jan. 27, 2015. All of these US Patents are incorporated by reference in their entirety.

A biopsy site marker is used to identify a biopsy site after a biopsy procedure. Generally, marker delivery devices use two types of needles. A first type of needle has an aperture at the end of a needle, and a second type of needle has a lateral aperture. There are two types of marker delivery devices that correspond with the two types of needles; end-deploy marker delivery devices and side-deploy marker delivery devices. End-deploy marker delivery devices deploy through an aperture in the distal end of the needle but require using a different introducer. Using a different introducer makes it more difficult for the operator to accurately deploy marker in an exact biopsy location. Side-deploy marker delivery devices can deploy a marker through the needle that took the biopsy sample. Side-deploy marker delivery devices can be more difficult to use because a marker can snag on the lateral aperture of the needle or a push rod can also get snagged on the lateral aperture and be difficult to withdrawal the marker delivery device.

Although marker delivery devices having a side-deploy configuration can have some drawbacks, they are nonetheless desirable because marking directly through the needle while it is still in position maintains the location where the biopsy sample was taken. A need exists for a marker delivery device capable of deploying through both end-deploy needles and side-deploy needles. Both end-deploy needles and side-deploy needles have advantages and disadvantages. Additionally, it would be desirable to combine elements of side-deploy marker delivery devices and end-deploy marker delivery devices into a single device.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings in which like reference numerals identify the same elements. In the drawings, some components or portions of components are shown in phantom as depicted by broken lines.

Figures 1A, 1B, 1C:
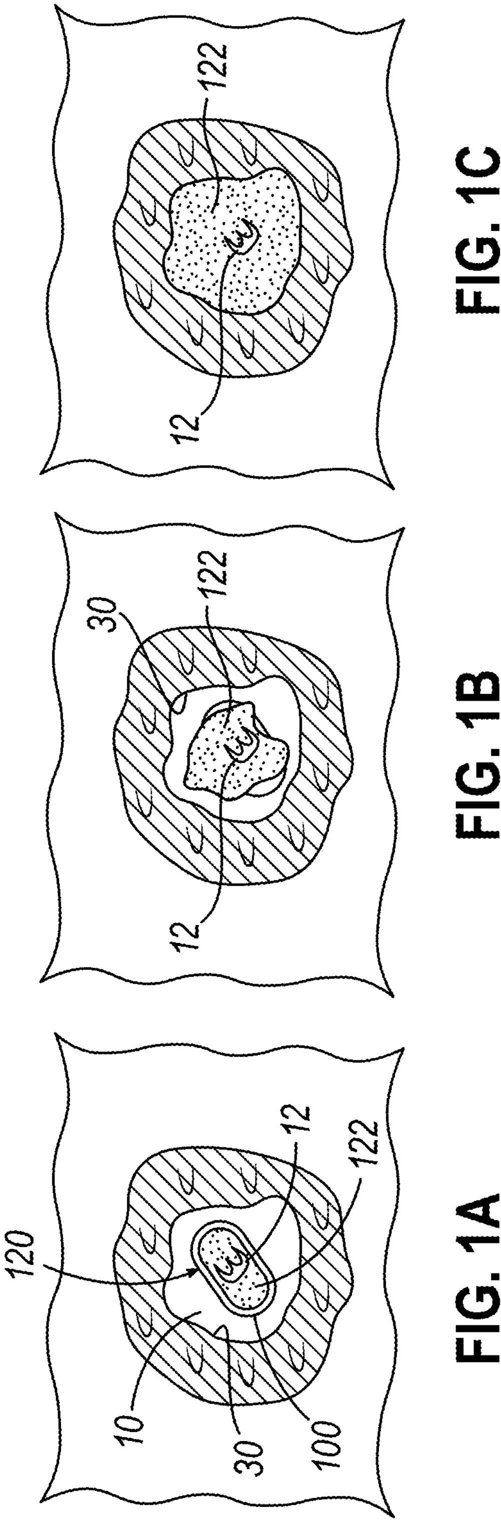
FIGS. 1A, 1B, and 1C show exemplary aspects of placement of a biopsy site marker, in accordance with aspects of the present disclosure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description, serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a grip. Thus, an end effector is distal with respect to the more proximal grip. It will be further appreciated that, for convenience and clarity, spatial terms such as "axial," and "longitudinal" also are used herein for reference to relative positions and directions. However, surgical instruments are used in many orientations and positions, and these terms are not intended to be limiting and absolute.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable for the marker to remain visible under ultrasound. It may also be desirable to make the marker readily identifiable relative to other structural features of a patient. For instance, it may be desirable for the marker to be distinguishable under ultrasound visualization from microcalcifications to avoid inadvertently characterizing the marker as a microcalcification during subsequent ultrasonic examinations. Generally, microcalcifications are used in the field to identify suspicious lesions or masses. Thus, it is generally desirable for the ultrasound view to be distinguishable as a marker and not inadvertently identified as a new mass.

I. Exemplary Marker

Aspects presented herein relate to devices and procedures for manufacturing a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. As will be described in greater detail below, marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials.

In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, marker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured, and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

The hydration of the marker material (122) of carrier (120) by the natural moisture of the tissue surrounding it causes expansion of the polymer and thus minimizes the risk of migration. The growing hydrogel based marker material (122) centers marker (100) in the biopsy cavity as it grows. As the hydrogel expands, naturally-present moisture from the surrounding tissue, the hydration enables increasing sound through transmission, appears more and more hypoechoic and is easy to visualize on follow up ultrasound studies.

The hydrated hydrogel marker material (122) of carrier (120) may also be used to frame permanent marker (12). The hypoechoic nature of the hydrated marker material (122) enables ultrasound visibility of the permanent marker (12) within the hydrogel hydrated marker material (122) because the permanent marker (12) is outlined as a specular reflector within a hypoechoic hydrated marker having a water-like nonreflective substrate.

II. Exemplary Marker Delivery Device

Figure 2:
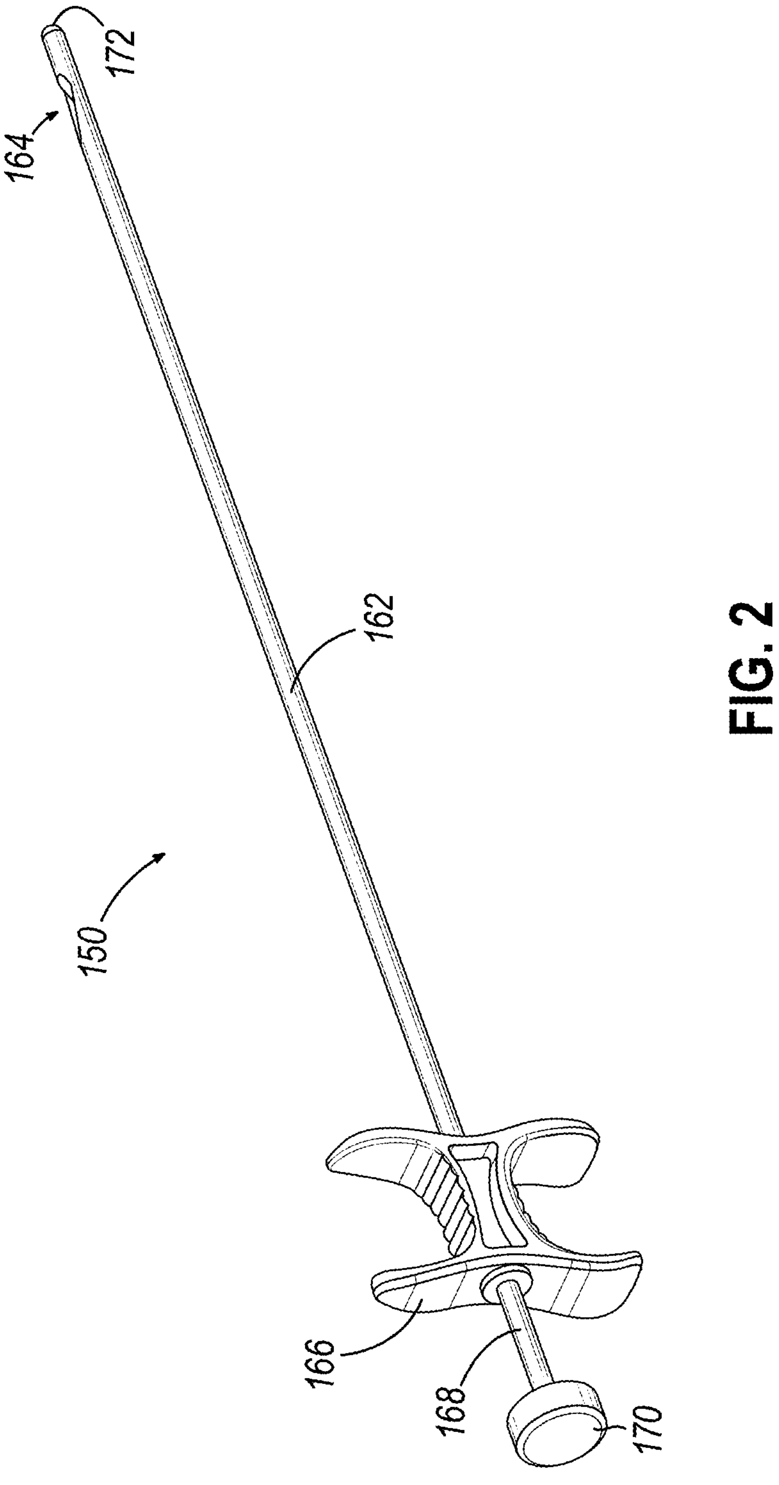
FIG. 2 depicts a perspective view of an exemplary marker delivery device.

In some examples it may be desirable to deploy marker (100) described above within the body cavity (30) using certain marker delivery devices. For instance, FIGS. 2 and 3 show an exemplary marker delivery device (150) which includes an elongate outer cannula (162) having a marker exit, such as side opening (164) formed adjacent to, but spaced proximally from, the distal end of the cannula (162).

A grip (166) can be provided at the proximal end of cannula (162). A push rod (168) can be provided, with push rod (168) extending coaxially in cannula (162) such that push rod (168) is configured to translate within cannula (162) to displace one or more markers through side opening (164) (see FIG. 3). Rod (168) may have sufficient rigidity in compression to push a marker from an internal lumen (165) of cannula (162) out through opening (164), yet be relatively flexible in bending. A plunger (170) is coupled at the proximal end of rod (168) for forcing rod (168) distally in cannula (162) to deploy a marker out of cannula (162).

A user may grasp grip (166) with two fingers and may push on plunger (170) using the thumb on the same hand, so that marker delivery device (150) is operated by a user's single hand. A spring (not shown) or another feature may be provided about rod (168) to bias rod (168) proximally relative to grip (166) and cannula (162).

Figure 3:
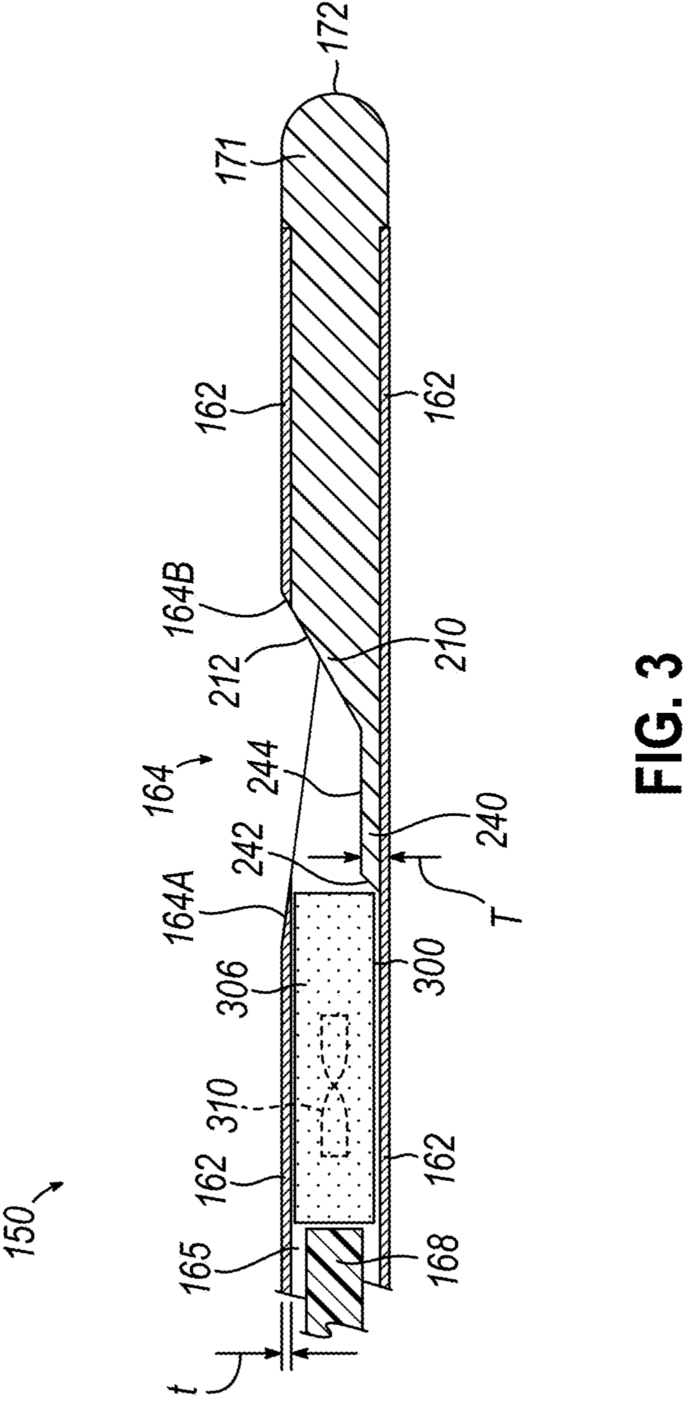
FIG. 3 depicts a side cross-sectional view of the marker delivery device of FIG. 2.

FIG. 3 shows a cross-sectional view of a distal portion of the marker delivery device (150). As can be seen, a biopsy marker (300), similar to marker (100) described above is disposed within internal lumen (165) of cannula (162). In the present example, marker (300) comprise a biodegradable or otherwise resorbable marker material (306), such as a generally cylindrically shaped body of collagen, hydrogel, or etc., and a metallic, generally radiopaque permanent marker or marker element (310) (shown in phantom) disposed within or otherwise carried by marker material (306).

Cannula (162) may be formed of any suitable metallic or non-metallic material. In some versions, cannula (162) is formed of a thin walled hollow tube formed of a suitable medical grade plastic or polymer. One suitable material is a thermoplastic elastomer, such as Polyether block amide (PEBA), such as is known under the tradename PEBAX. Cannula (162) may be formed of PEBAX, and may be substantially transparent to visible light and X-ray.

Side opening (164) may be formed by cutting away a portion of the wall of cannula (162). Side opening (164) communicates with an internal lumen (165) of cannula (162). Side opening (164) may extend axially (in a direction parallel to the axis of lumen (165)) from a proximal opening end (164A) to a distal opening end (164B), as illustrated in FIG. 3.

In the present example, distal tip (172) extends from the distal end of cannula (162) and is rounded as shown in FIG. 3. Referring to FIG. 3, the distal end of cannula (162) is closed by a unitary endpiece (171), with a portion of endpiece (171) extending into internal lumen (165) of cannula (162). Endpiece (171) may be a molded or cast component. Endpiece (171) comprises a tip (172), a ramp (210) having a ramp surface (212), and a marker engaging element (240). Ramp surface (212) aids in directing marker (300) from internal lumen (165) through side opening (164). Marker engaging element (240) helps to retain marker (300) in internal lumen (165) until the user intends to deploy marker (300).

Marker engaging element (240) is disposed within internal lumen (165), and at least a portion of marker engaging element (240) is disposed distally of proximal end (164A) of side opening (164). Marker engaging element (240) extends along a portion of the floor of cannula (162) under opening (164) such that marker engaging element (240) is positioned to reinforce the portion of cannula (162) in which opening (164) is formed. For instance, by positioning marker engaging element (240) underneath opening (164), as shown in FIG. 3, element (240) helps to stiffen cannula (162) in the region where wall of cannula (162) is cut to form opening (164). As shown in FIG. 3, marker engaging element (240) extends from the proximal most portion of ramp surface (212) and does not extend proximally of side opening (164), though in other embodiments, a portion of element (240) may extend proximally of opening (164).

As shown in FIG. 3, marker engaging element (240) is in the form of a step having a generally uniform thickness (T) along element's (240) axial length, except that element (240) has a tapered proximal end (242). Tapered proximal end (242) forms an included angle with the longitudinal axis of lumen (165) (included angle with a horizontal line in FIG. 3) of about 45 degrees, while ramp surface (212) forms an included angle with the longitudinal axis of about 30 degrees. Of course, any number of other suitable angles may be used.

As shown in FIG. 3, an upwardly facing surface (244) (surface facing opening (164)) of marker engaging element (240) extends distally to contact ramp surface (212), so that there is not a space or gap between surface (244) and ramp surface (212). Such an arrangement is advantageous to reduce the possibility that marker (300), upon moving past marker engaging element (240), may become lodged between marker engagement element (240) and ramp (212). In some versions, marker engaging element (240), ramp (210), and/or tip (172) are formed of, or include, a material that is relatively more radiopaque than the wall of cannula (162). For instance, where element (240), ramp (210), and tip (172) are formed as an integral endpiece (171), endpiece (171) may include a radiopaque additive, such as barium sulfate. For instance, endpiece (171) may be a component molded of PEBAX, with about 20 percent by weight barium sulfate added to the molten PEBAX mold composition. The relatively more radiopaque marker engaging element (240), ramp (210), and tip (172) may be useful in distinguishing the position of those components using radiographic imaging. Also, where ramp (210) and/or step of engaging element (240) are positioned in association with opening (164), the addition of a radiopaque material can help identify the position of opening (164), and the position of marker (300) relative to opening (164) before, during, or after deployment of marker (300).

Figure 4:
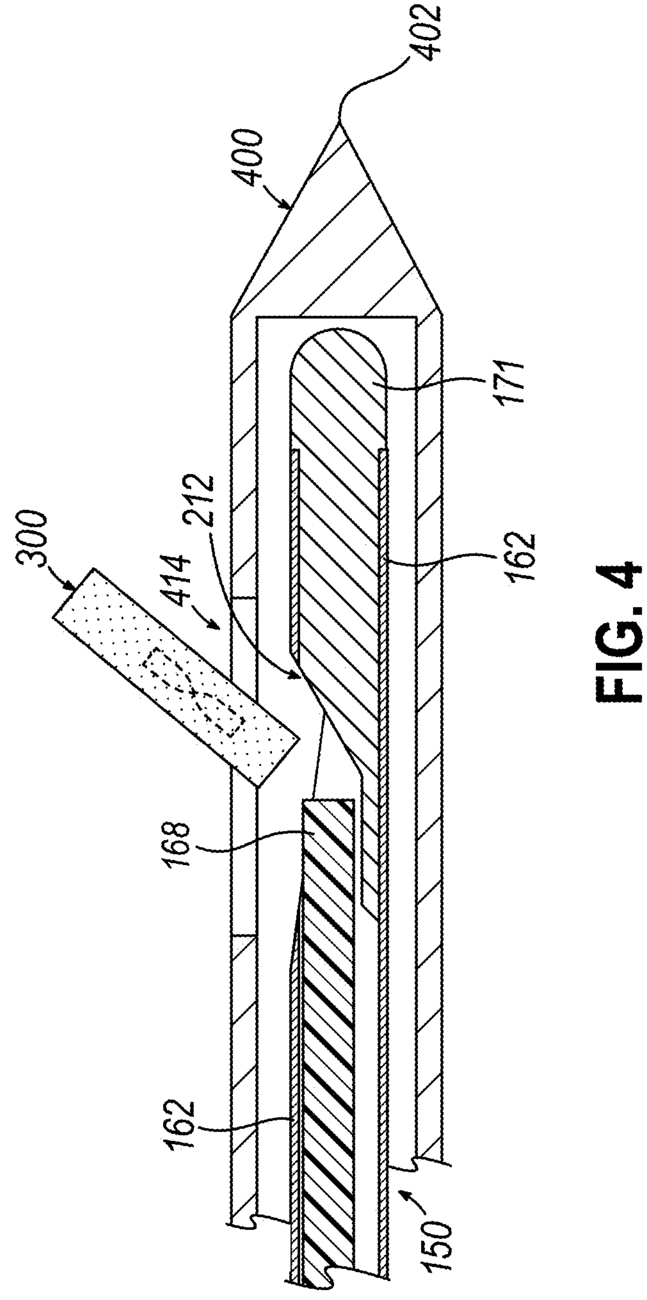
FIG. 4 depicts a cross-sectional view of a marker being deployed from the distal portion of the marker delivery device of FIG. 1 and through a lateral aperture in a biopsy needle to mark a biopsy site.

Referring to FIG. 4, marker delivery device (150) is used to deploy a marker (300) to mark a biopsy location within a patient. In FIG. 4, a cannular biopsy needle (400) is shown having a closed distal end with piercing tip (402) and a lateral tissue receiving aperture (414). Marker delivery device (150) is introduced to a biopsy site through biopsy needle (400), which may be the same needle (400) used to collect a tissue sample from the biopsy site. Biopsy needle (400) may be of the type used with single insertion, multiple sample vacuum assisted biopsy devices. Several such biopsy devices are disclosed in the various patents and patent applications that have been referred to and incorporated by reference herein, though other biopsy devices may be used.

III. Exemplary Shape Memory Marker Deployment Device

In some examples, it may be desirable to side-deploy a marker from a side aperture of a needle. In particular, in some examples it may be desirable to deploy a marker through a marker delivery device similar to marker delivery device (150) described above, but utilizing an inner cannula with a bend. In such examples, deployment from a marker delivery device that allows the marker to make a smooth transition from being translated longitudinally to transverse through the side aperture of the needle may be desirable. A bend in the inner cannula will ensure delivery of the marker without the marker or push rod snagging on the aperture which has sharp edges. While various examples of suitable devices for providing marker deployment through the distal end of a marker delivery device are described herein, various alternative configurations may be used as will be apparent to those of ordinary skill in the art in view of the teachings herein.

Figure 5A:
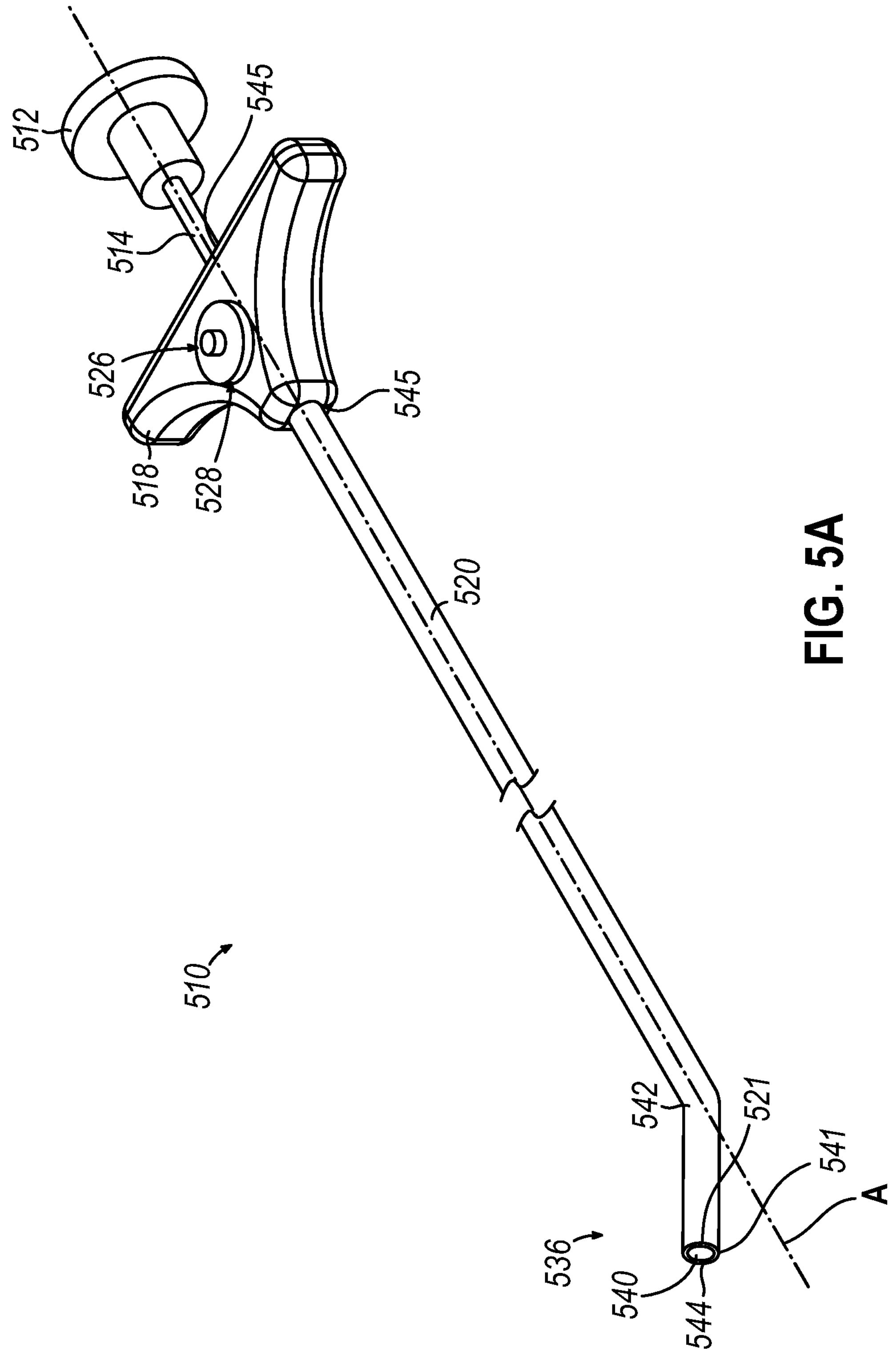
FIG. 5A depicts a perspective view of an inner cannula assembly of another exemplary marker delivery device.
Figure 5B:
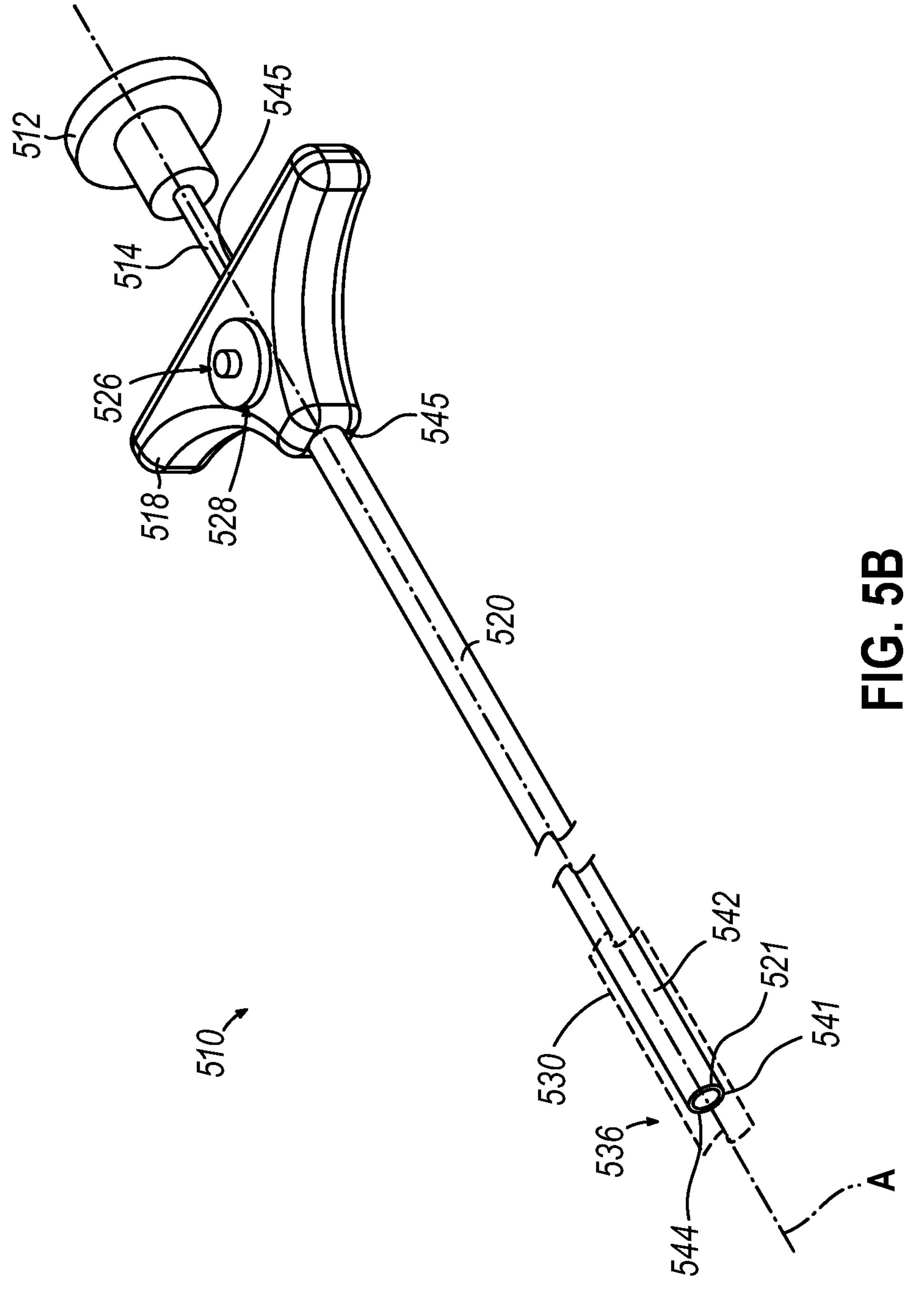
FIG. 5B depicts a perspective view of the inner cannula assembly of FIG. 5A partially inserted into a portion of an outer cannula (shown in phantom).
Figure 6:
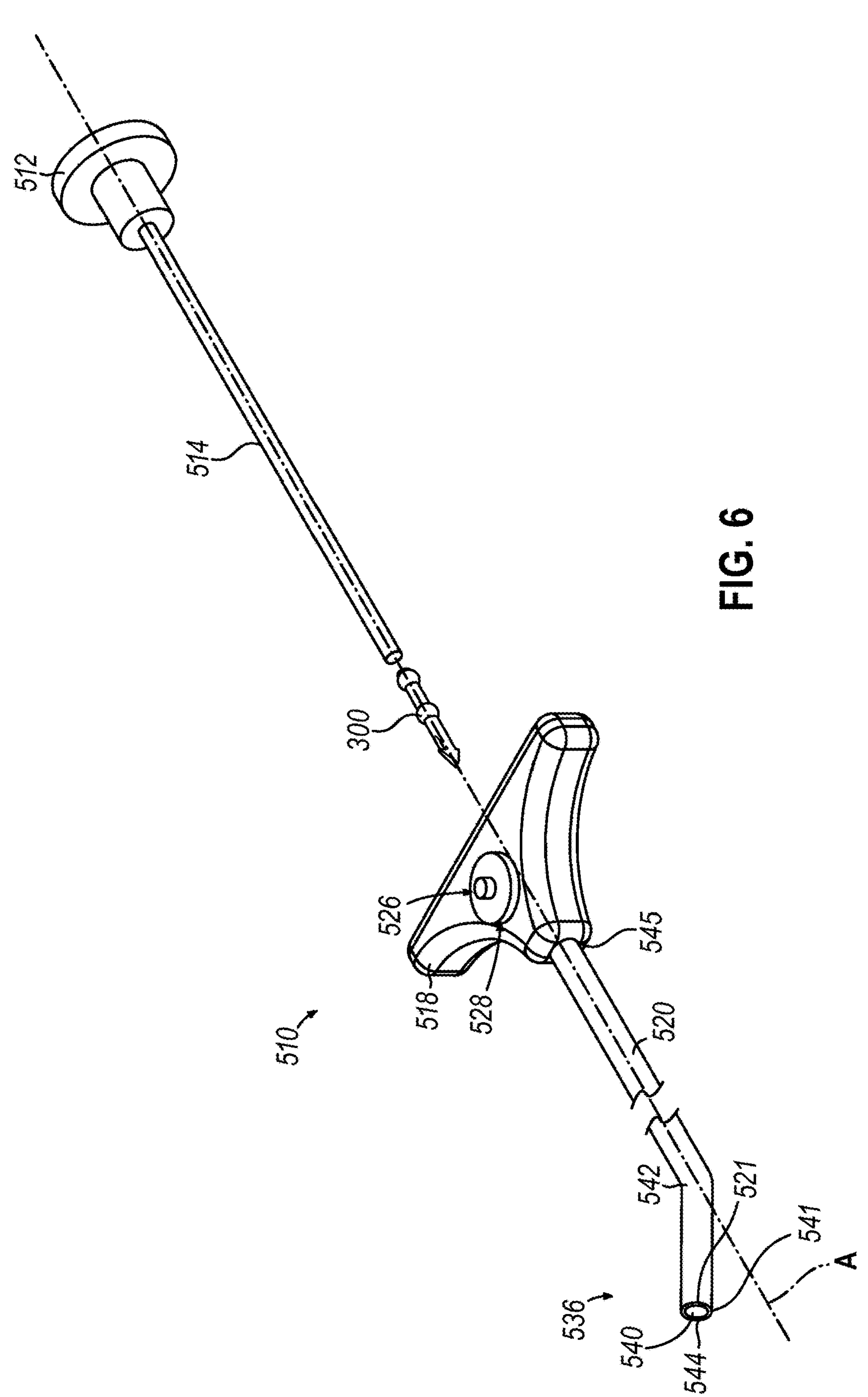
FIG. 6 depicts a partially exploded perspective view of the inner cannula assembly of FIG. 5A.

FIGS. 5A, 5B and 6 shows an exemplary marker delivery device (510) that is generally configured as an end deploy marker delivery device that can be used in side-deployment contexts such as through a lateral aperture of a biopsy needle. It should be understood that marker delivery device (510) is substantially similar to marker delivery device (150) described above except where explicitly noted herein. Like with marker delivery device (150), marker delivery device (510) has a cannula (520), a grip (518), a push rod (514), a plunger (512) and a marker exit (540). Additionally, marker delivery device (510) has inner cannula (520) extend distally from the user, grip (518) is configured for the operator to hold and manipulate the marker delivery devices (510), and plunger (512) is operatively coupled to push rod (514) to aid the operator in translating marker (300) through marker exit (540) located distal from the operator similar to marker delivery device (150).

However, unlike marker delivery device (150), marker delivery device (510) of the present example includes marker exit in the form of a distal aperture (540) that is located at an inner cannula distal end (544). Marker delivery device (510) also has a bend (542) that is angularly displaced from axis (A) to allows a marker (300) to be deployed through a side aperture (554) without removing a needle (552) from the patient see FIG. 9A. Axis (A) extends generally away from the operator. Inner cannula assembly (510) may also be used with an end deploy needle (not shown).

FIG. 5A shows marker delivery device (510). Marker delivery device includes an inner cannula (520), a push rod (514) a plunger (512), and a grip (518).

Figure 7:
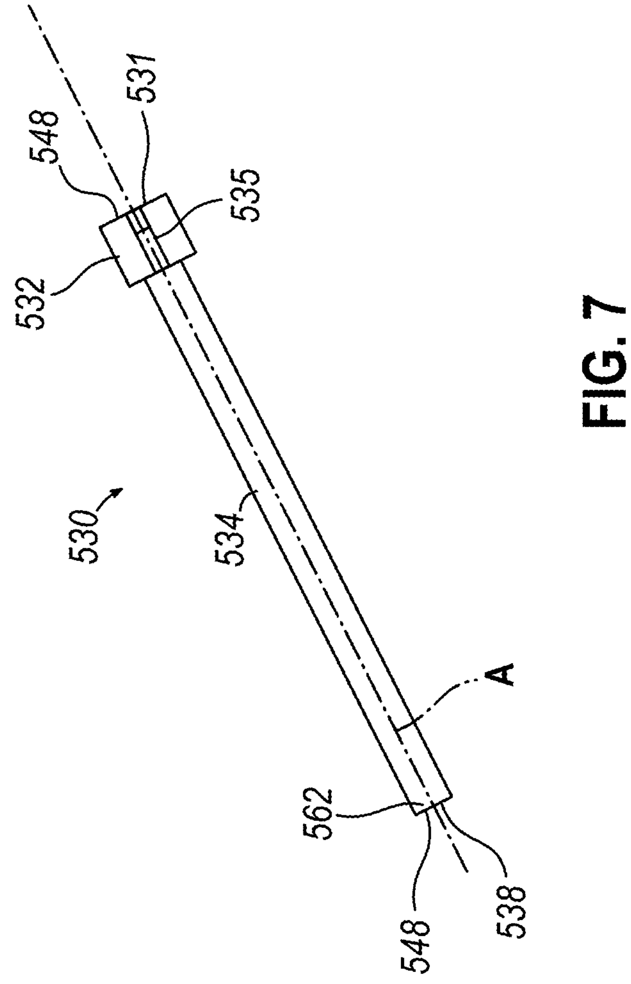
FIG. 7 depicts a perspective view of an outer cannula assembly of a marker delivery device formed by the inner cannula assembly of FIG. 5A and the outer cannula.

Inner cannula (520) is generally tubular in shape. Inner cannula (520) can have other shapes such as an elongate cross-section that is rectangular, square, triangular, or oval in shape. Inner cannula (520) extends distally from inner cannula proximal end (545) to inner cannula distal end (544). Inner cannula (520) includes a bend (542) located in distal portion (536), and distal aperture (540) at distal end (544). Inner cannula has a inner lumen (541) that extending from proximal end of grip (518) generally along axis (A) following resilient curve (542) that angularly deviates from axis (A) to distal aperture (540) at distal end (544). Axis (A) generally extends distally away from the operator from grip (518) along inner cannula (520) to distal portion (536). As will be described in greater detail below, inner cannula assembly (510) is sized to fit within outer lumen (548) of outer cannula (534) (see FIG. 7).

Plunger (512) is operatively connected to push rod (514). Plunger (512) allows a user comfortably to push upon a greater surface area than push rod (514). Push rod (514) is inserted coaxially and distally through an inner cannula proximal end (545) into a inner lumen (541) of inner cannula (520). Push rod (514) is used to translate marker (300) through distal aperture (540). Push rod (514) is sized in diameter to fit within inner lumen (541) of inner cannula (520). Push rod (514) will also be sized in length to translate a marker (300) through inner lumen (541) and displace marker (300) through distal aperture (540). Push rod (514) may be constructed of a rigid, yet flexible material such as plastic, hard rubber, aluminum, or stainless steel. Push rod (514) may also be constructed of a shape memory alloy or of a material having basic resilient properties to aid deployment through bend (542).

Grip (518) can be provided at inner cannula proximal end (545). Grip (518) is sized and configured to be grasped and operated by a single hand of an operator. Inner cannula proximal end (545) may be coaxially disposed in grip (518) along axis A or inner cannula proximal end (545) may be operatively attached to distal end of grip (518).

Figure 9A:
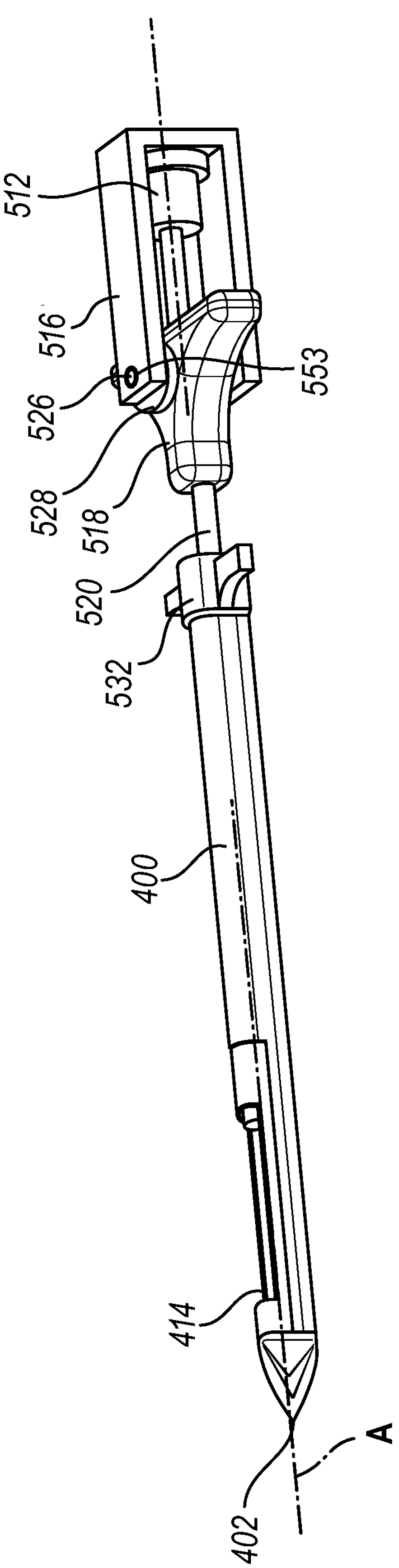
FIG. 9A depicts a perspective view of the marker delivery device formed by the inner cannula assembly of FIG. 5A and the outer cannula of FIG. 7 fully inserted into a needle with the inner cannula partially inserted into the outer cannula.

Grip can be fitted with a push rod guard (516) (see FIG. 9A). Push rod guard (516) is operatively attached to grip (518) by a guard aperture (553) (see FIG. 9A). Guard aperture (553) is rotatably coupled to guard attachment nub (526). Push rod guard (516) rides on guard attachment races (528). Guard attachment races (528) may have a locking feature (not shown) to maintain the push rod guard (516) in the first position or second position. This locking feature may be in the form of a detent feature or a locking pin. This locking feature keeps push rod guard (516) from inadvertently being rotated.

FIG. 5A shows bend (542) in a relaxed state. In the relaxed state, bend (542) deflects away from axis (A). Bend (542) may bend from 0 to 90 degrees from axis (A). Bend (542) may have a sharp bend or a gradual bend away from axis (A). Bend (542) having a gradual arcuate shape may prevent marker (300) or push rod (514) from binding into sidewall (521).

Inner cannula (520) of the present example can be constructed as a shape memory alloy. In some examples, a suitable shape memory alloy can be configured to transition from a first shape at a first temperature (FIG. 5B) to a second shape at a second temperature (FIG. 5A), although temperature responsiveness is not required. Inner cannula (520) can be constructed of memory based alloys such as nitinol (ni-titanium), or copper-aluminum-nickel. Shape memory alloys can also be created by alloying zinc, copper, gold and iron. The shape memory alloy can be two-way or one-way. Two-way shape memory alloys "remember" a first shape, and a second shape. The two-way shape memory alloy transitions from a first shape to a second shape at a transition temperature. When the shape memory alloy is below the transition temperature the shape retains the first shape. When the shape memory alloy is above the transition temperature the shape memory alloy transitions to a second shape. When a two-way shape memory alloy returns to the temperature below the transition temperature, the first shape is restored. A one-way shape memory alloy only transitions from a first shape to a second shape once the one-way shape memory alloy reaches the transition temperature. A one-way shape memory alloy will not transition back to the first shape when the first temperature is restored.

In examples where inner cannula (520) is configured with two-way shape memory properties, inner cannula (520) would have two distinct shapes. FIG. 5A shows the arcuate shape at a higher temperature and FIG. 5B shows the straight shape at the lower temperature. This shape memory alloy may have a transition temperature that corresponds with the temperature of a patient's body. An inner cannula (520) having shape memory properties would be stored at a temperature lower than the temperature of a patient's body. This would allow inner cannula (520) to be inserted into outer cannula (534) in the straight configuration at a temperature less than one that corresponds with the temperature of a patient's body.

Other embodiments may utilize other suitable sterile, basic resilient materials to construct inner cannula (520). Basic resilient materials are materials that have more than one shape. Basic resilient materials will transition between shapes when acted upon by tangential stress about axis (A). This transition takes place in bend (542). Basic resilient materials will be arcuate in the relaxed shape, and straight in the stressed shape. Basic resilient materials are any suitable material that can retain its shape after being stressed. When using basic resilient materials, inner cannula (520) is put in a state of tension when inserted into outer lumen (548). Bend (542) straightens, when within outer lumen (548), but regains its relaxed shape when no longer held straight by an outer cannula sidewall (562). When inserted into outer cannula (534), inner cannula (520) conforms to the shape of outer cannula (534) and the angle of the bend (542) reduces, allowing inner cannula to pass through outer cannula (534).

FIG. 6 shows an exemplary embodiment of an outer cannula assembly (530). The outer cannula includes an outer cannula (534) and handle (532). Outer cannula (534) is generally tubular and thin walled in construction. Outer cannula (534) has an outer lumen (548) that extends distally along longitudinal axis (A) from an outer cannula proximal end (531) to an outer cannula distal end (538). Outer cannula (534) also has a distal aperture (536) located at outer cannula distal end (538). Handle (532) may include handle nubs (535) that aid the operator in gripping handle (532). Handle (532) may also have a locking feature (not shown). Locking feature may be a detent, a collet, or a thread containing a compressible member. Locking feature is configured to slidably couple with marker delivery device (510) see FIG. 5A within outer cannula assembly (530).

Figure 8A:
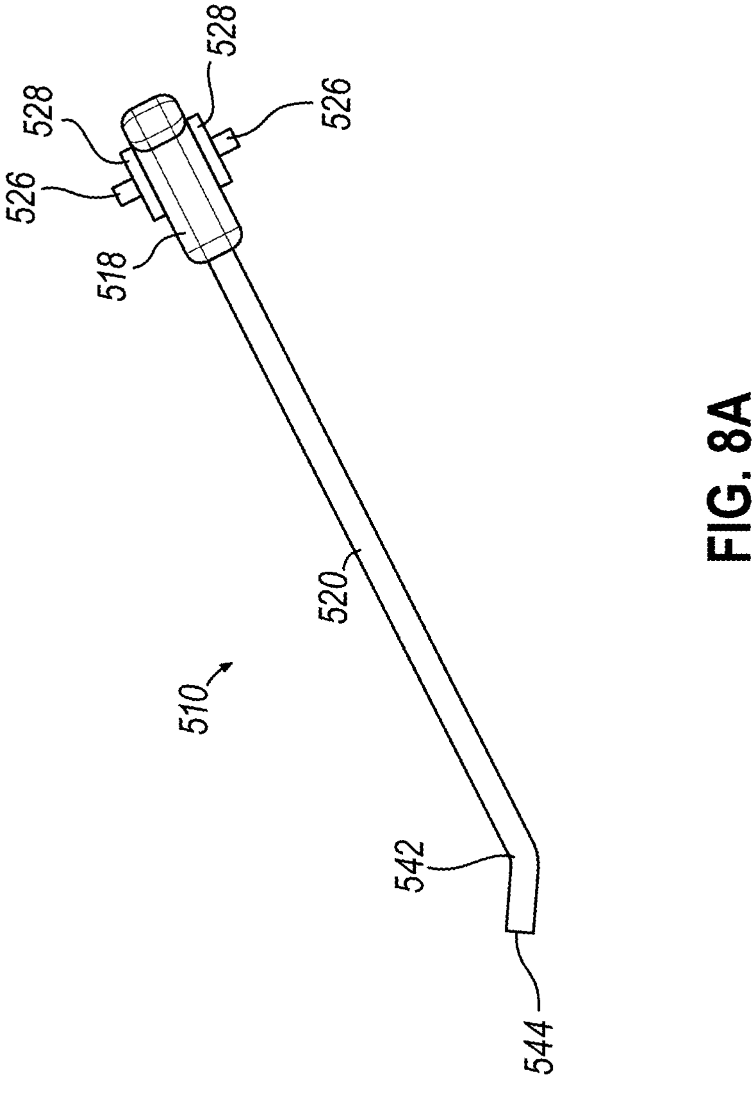
FIG. 8A depicts a perspective view of an inner cannula of the inner cannula assembly of FIG. 5A.
Figure 8B:
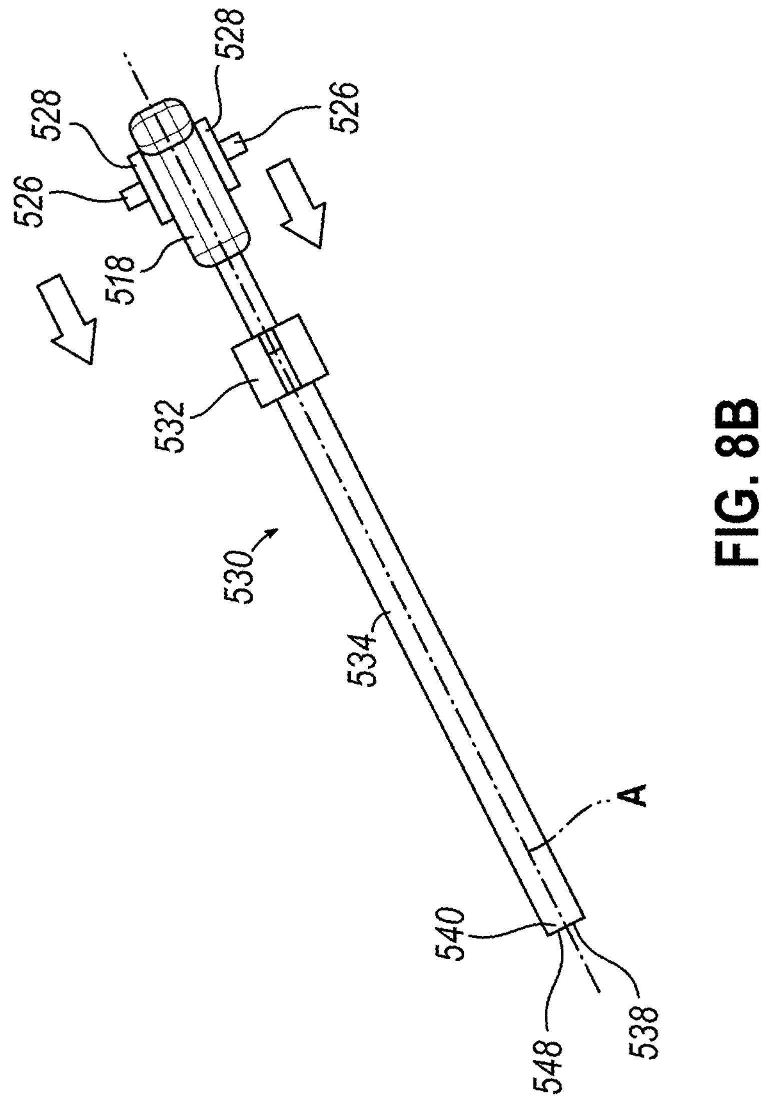
FIG. 8B depicts a perspective view of the inner cannula of FIG. 8A partially inserted into the outer cannula of FIG. 7 such that the inner cannula is held in a stressed configuration.
Figure 8C:
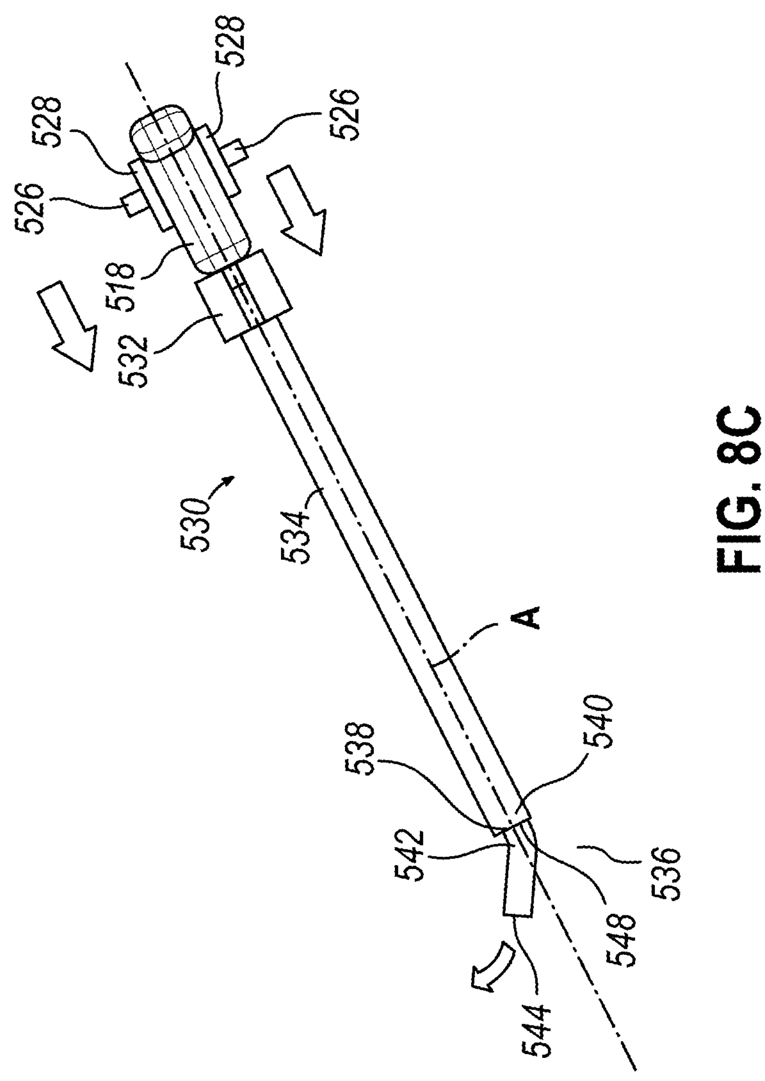
FIG. 8C depicts another perspective view of the inner cannula of FIG. 8A fully inserted into outer cannula of FIG. 7.

FIGS. 8A-8C shows marker delivery device (510), being inserted into the outer cannula assembly (530) described above. FIG. 8A shows marker deployment device (510) before insertion into outer cannula assembly (530). Inner Cannula (520) is in the relaxed state. Bend (542) is in an arcuate shape when in the relaxed state. Grip (518) includes a guard attachment nub (526) and a guard attachment race (528). Guard attachment nub (526) and guard attachment race (528) are configured to receive pushrod guard shown in FIG. 9A.

FIG. 8B shows marker delivery device (510) partially and coaxially inserted into outer lumen (548). Inner cannula distal end (544) is inserted into outer cannula proximal end (531). Handle (532) locking feature (not shown) can lock marker delivery device (510) into outer cannula assembly (530). Bend (542) will conform to the straight shape of outer lumen (548) when inner cannula assembly (510) is partially inserted into outer cannula assembly (530).

FIG. 8C shows marker delivery device (510) fully inserted into second bore (548) of outer cannula assembly (534) along longitudinal axis (A). Distal portion (536) of inner cannula extends through distal aperture (540) located at outer cannula distal end (538), and distal portion (536) is no longer within outer lumen (548) of outer cannula (534). Bend (542) becomes arcuate in shape. This arcuate shape deviates from axis (A). The arcuate shape is either formed in response to temperature of the patient's body, or in response to inner cannula (520) having inherent resiliency and distal portion (536) being no longer contained within outer lumen (548).

FIGS. 9A-9D shows marker delivery device being used with needle (400) of FIG. 4 to deploy marker (300). Outer cannula assembly (530) is inserted into the proximate end of needle (400). Marker delivery device (510) is partially and coaxially inserted into outer lumen (548) of outer cannula assembly (530) with pushrod guard (516) in a first position. In the first position, plunger (512) may not be inadvertently bumped, and prematurely deploying marker before the operator intends to deploy marker (300). Locking device (not shown) in handle (532) may secure marker delivery device (510) to outer cannula assembly (530). Additionally, handle (532) may secure outer cannula assembly (530) to needle (400).

Figure 9B:
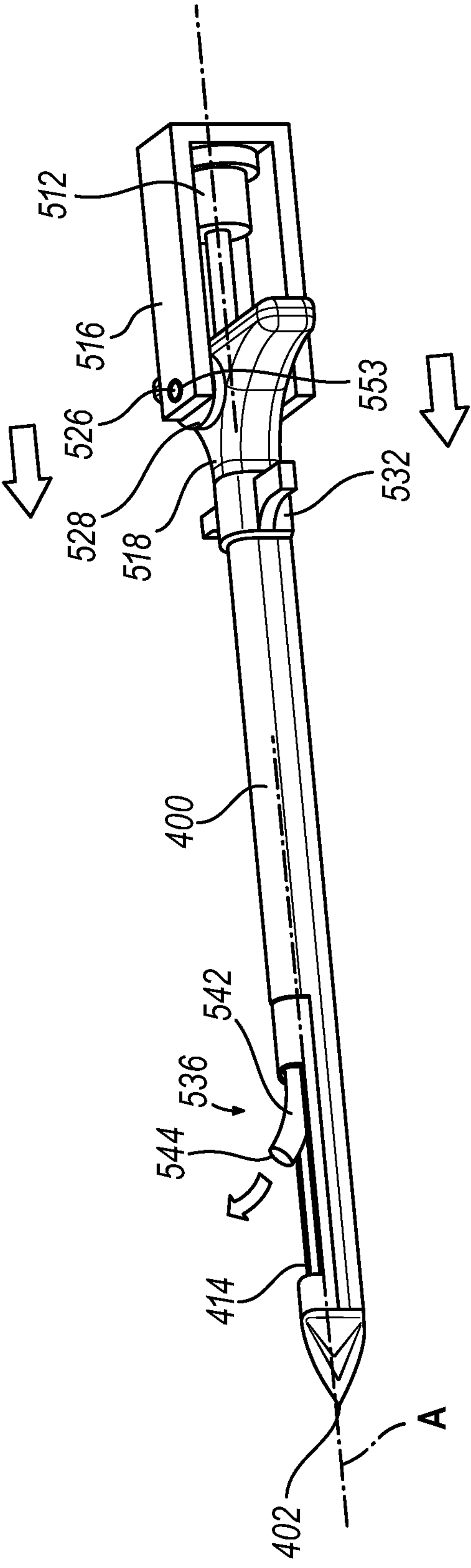
FIG. 9B depicts another perspective view of the marker delivery device of FIG. 9A with inner cannula fully inserted into outer cannula.

FIG. 9B shows grip (518) of marker delivery device (510) being pushed towards handle (532). Distal portion (536) is translated longitudinally away from the operator and protrudes from lateral aperture (414) at bend (542). Bend (542) departs from the axis (A) and protrudes through side aperture (414) to facilitate side deployment of marker (300). Bend (542) regains its arcuate shape either due to the shape memory alloy reacting to the temperature of the body or the basic resilient material regaining its shape because the basic resilient material is no longer confined under tension in outer lumen (548).

Figure 9C:
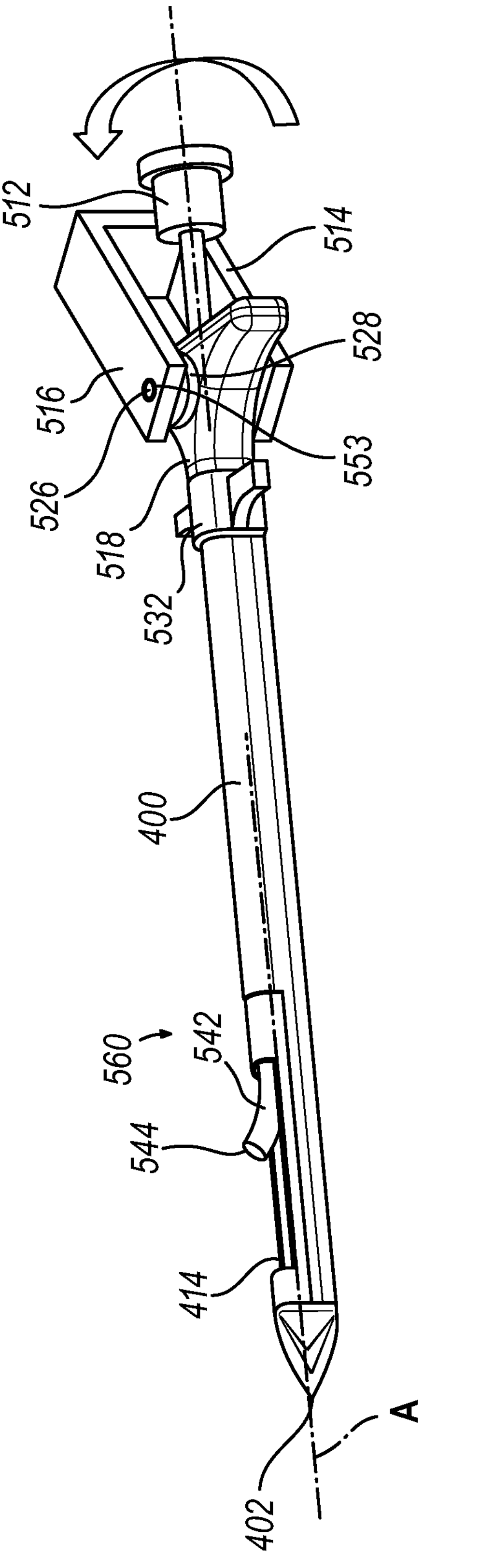
FIG. 9C depicts still another perspective view of the marker delivery device of FIG. 9A, with a push rod guard disengaged.

FIG. 9C shows pushrod guard (516) being rotated in an arcuate manner about guard attachment nubs (526), tangential to axis (A) from first position to a second position. Pushrod guard (516) rides on guard attachment races (528). In second position of the pushrod guard (516) the operator may translate plunger (512) to deploy a marker (300).

Figure 9D:
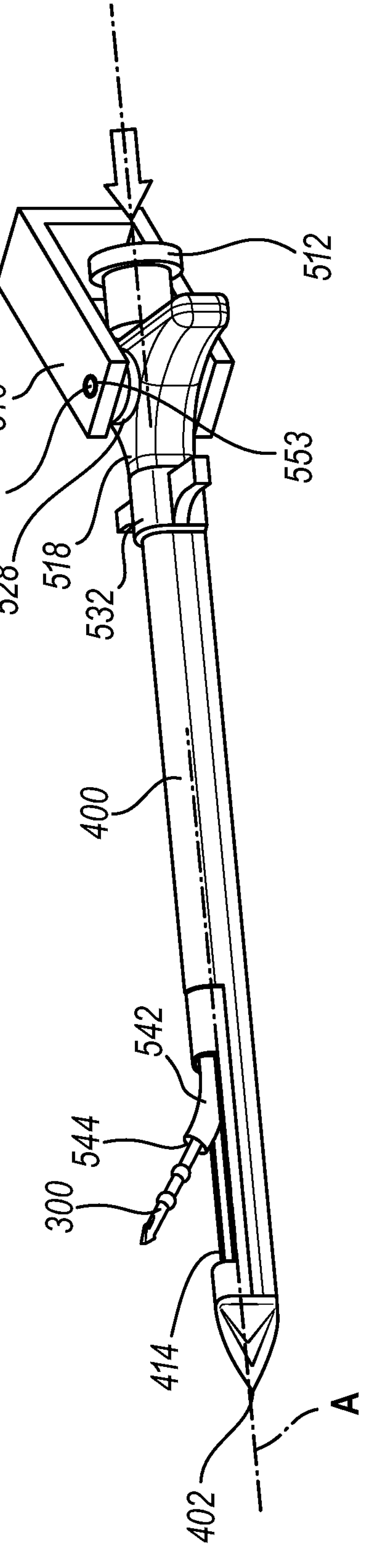
FIG. 9D depicts yet another perspective view of the marker delivery device of FIG. 9A, with the push rod deploying a marker.

FIG. 9D shows pushrod guard (516) in second position, and plunger (512) being translated distally away from the operator. The operator translates plunger (512) with a thumb or finger. Plunger (512) translates push rod (514) distally. Before plunger (512) may be pushed by the operator, marker (300) must be installed in inner lumen (541). Marker (300) is installed by translating plunger (512) proximally until push rod (514) is removed from inner lumen (541). After push rod (514) is removed, marker (300) may be inserted into inner lumen (541). Once marker (300) is inserted into inner lumen (541), push rod (514) may be partially inserted into inner lumen (541) and plunger (512) may be translated distally away from the operator. Marker (300) may also be inserted into inner lumen (541) before marker delivery device (510) is inserted into needle (400). Once marker (300) is inserted, operator pushes plunger (512) which translates push rod (514) distally, translating marker (300) distally through inner lumen (541) of inner cannula (520). Push rod (514) deploys marker (300) through distal aperture (540) facilitating side deployment of marker (300).

Figure 10:
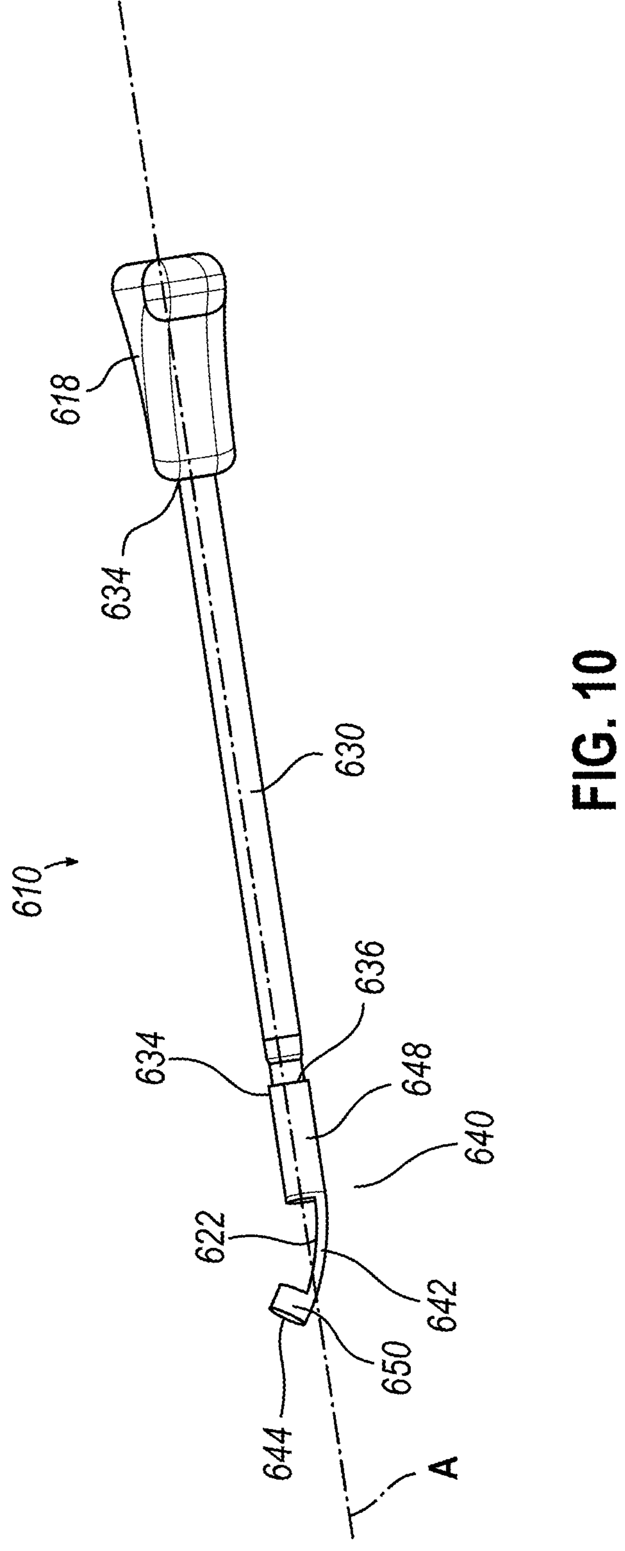
FIG. 10 depicts another exemplary alternative marker delivery device.

FIG. 10 shows an alternate exemplary embodiment of marker delivery device (610). Marker delivery device (610) like marker delivery device (510) has a grip (618), an inner cannula (630), and a bend (622). Marker delivery device (610) differs from marker delivery device (510) in that marker delivery device (610) has two sections of inner cannula (630, 640). Also, marker delivery device (610) has a bend (622) that is that can be non-tubular in shape.

Marker delivery device (610) includes a first inner cannula (630) and a second inner cannula (640). First inner cannula (630) is located more proximally than second inner cannula (640) in relation to the operator. First inner cannula proximal end (634) is operatively attached to grip (618). First inner cannula distal end (636) is operatively attached to second inner cannula proximal end (634). First inner cannula distal end (636) may be permanently affixed or removably affixed to second inner cannula proximal end (634). Second inner cannula (640) may be removable, by any suitable fastener such as threads or a pin.

First inner cannula (630) may have properties of rigidity. First inner cannula (630) will be constructed of materials having rigidity such as plastics, surgical stainless steel, and hard rubber. Second inner cannula (640) may be constructed of a material having basic resilient properties or a shape memory alloy described above.

Second inner cannula (640) can be tubular in shape only at an attachment end (648) and at deployment end (650). Bend (642) may have a partial tubular configuration where less than 360 degrees of the tubular shape is present. Bend (642) may be configured with a band (622) of material attaching attachment end (648) to deployment end (650). Band (622) can be flat or arcuate in shape. Second inner cannula (640) can also be continuously tubular in shape (not shown) from second inner cannula proximal end (634) to distal end (644).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: an outer cannula, wherein the outer cannula includes an outer lumen, wherein the outer lumen extends distally along the longitudinal axis from a handle to an open outer cannula distal end; an inner cannula assembly including an inner cannula, wherein the inner cannula is disposed within the outer lumen and extends distally along a longitudinal axis from a grip to an open distal end, wherein the inner cannula has a resilient portion located proximate to the open distal end, wherein the resilient portion is configured to move between a stressed position when engaged with the outer cannula and in a relaxed position when disengaged with the outer cannula; and a plunger operatively connected to a push rod disposed within an inner lumen of the inner cannula, wherein the push rod is configured to deploy a marker through the open distal end.

Example 2

The marker delivery device of Example 1, wherein the push rod is configured to move within the inner lumen to deploy the marker through a needle.

Example 3

The marker delivery device of any one or more of Examples 1 or 2, wherein the inner cannula is made from a shape memory alloy.

Example 4

The marker delivery device of Example 3, wherein the shape memory alloy is nitinol, or a copper-based alloy.

Example 5

The marker delivery device of Example 3 or 4, wherein the shape memory alloy is a two-way shape memory alloy.

Example 6

The marker delivery device of Example 3 or 4, wherein the shape memory alloy is a one-way shape memory alloy.

Example 7

The marker delivery device of any one or more of Examples 1 through 6, further comprising a guard having a first position and a second position, wherein the guard is configured to block access to the plunger in the first position, and the guard is configured to allow access to the plunger in the second position, wherein the plunger is operable to deploy a marker when the guard is in the second position.

Example 8

The marker delivery device of Example 7, wherein the guard has a retaining feature, wherein the retaining feature is a detent or a locking pin.

Example 9

The marker delivery device of any one or more of Example 1 through 8, wherein the push rod includes a shape memory alloy.

Example 10

The marker delivery device of any one or more of Example 1 through 9, wherein the push rod is made from a rigid material.

Example 11

The marker delivery device of any one or more of Examples 1 through 10, wherein the inner cannula has a cross-section that is round, oval, square, triangular, or rectangular.

Example 12

The marker delivery device of any one or more of Examples 1 through 11, wherein the handle including a locking feature.

Example 13

The marker delivery device of Example 12, wherein the locking feature is configured to slidably couple the inner cannula within the outer cannula.

Example 14

The marker delivery device of Examples 12 or 13, wherein the locking feature is configured to slidably couple the outer cannula within a needle.

Example 15

The marker delivery device of any one or more of Examples 1 through 14, wherein the outer cannula is movably coupled to the inner cannula to translate the inner cannula between a plurality of positions.

Example 16

The marker delivery device of Example 12 through 15, wherein the locking feature is in the form of a detent, collet, or threads containing a compressible member.

Example 17

The marker delivery device of any one or more of Example 1 through 16, wherein the resilient portion has a partial tubular shape.

Example 18

The marker delivery device of Example 1 through 17, wherein the inner cannula includes a first cannula portion extending distally along the longitudinal axis to a first cannula portion distal end, and a second cannula portion operatively connected to the first cannula distal end and extending distally generally along the longitudinal axis to the open distal end, wherein the second cannula portion includes an attachment end and a deployment end and the resilient portion therebetween the attachment end and the deployment end.

Example 19

The marker delivery device of Example 18, wherein the first cannula portion is removably attached to the second cannula portion by a thread or a pin.

Example 20

The marker delivery device of Example 18, wherein the first cannula portion is permanently attached to the second cannula portion.

Example 21

The marker delivery device of any one or more of Examples 1 through 17, wherein the resilient portion is comprised of a flat band of material having resilient properties operatively connecting an attachment end to a deployment end.

Example 22

A biopsy system comprising: an inner cannula assembly including a grip and an inner cannula, wherein the inner cannula extends distally along a longitudinal axis from the grip to an open distal end, wherein the inner cannula has a resilient portion located proximate to the open distal end, wherein the resilient portion has a natural position that deflects from the longitudinal axis and a stressed position that is straight, wherein the push rod is configured to deploy a marker through the open distal end; and an outer cannula disposed around the inner cannula, wherein the outer cannula defines an open distal end; and a needle disposed around the outer cannula, wherein the needle includes a side aperture, wherein the resilient portion protrudes from the side aperture when the inner cannula fully inserted into outer cannula.

Example 23

A method of deploying a biopsy marker to a biopsy site, comprising inserting an inner cannula into a biopsy needle while the inner cannula is in a first position relative to an outer cannula; and transitioning the inner cannula to a second position relative to an outer cannula to move an open distal end of the cannula to protrude out of a lateral aperture of the biopsy needle.

Example 24

The method of Example 23, further comprising: inserting a marker partially into an inner lumen of an inner cannula.

Example 25

The method of Example 24, further comprising inserting a push rod into the inner lumen of an inner cannula partially translating marker distally from the operator.

Example 26

The method of Example 25, further comprising inserting the outer cannula into the biopsy needle.

Example 27

The method of Example 26, further comprising rotating the guard to access a plunger.

Example 28

The method of Example 27, further comprising depressing the plunger deploying the marker into the body of the patient.

Example 29

A biopsy system, comprising: a push rod; an inner cannula assembly including a grip and an inner cannula, the inner cannula extending distally along a longitudinal axis from the grip to an open distal end, the inner cannula having a resilient portion located proximate to the open distal end, the resilient portion having a natural configuration and a stressed configuration, the natural configuration corresponding to the resilient portion being deflected from the longitudinal axis, the stressed configuration corresponding to the resilient portion extending generally along the longitudinal axis, the push rod being configured to deploy a marker through the open distal end of the inner cannula; an outer cannula disposed around the inner cannula and configured to transition the resilient portion of the inner cannula between the natural configuration and the stressed configuration; and a needle configured to receive the inner cannula and the outer cannula, the needle including a side aperture, the resilient portion being configured to position the open distal end thereof proximate the side aperture when the inner cannula and outer cannula are fully inserted into needle.

Example 29

The biopsy system of Example 29, the outer cannula being configured to transition the resilient portion of the inner cannula from the stressed configuration to the natural configuration when the inner cannula is fully inserted into the outer cannula.

Example 30

The biopsy system of Example 30, the outer cannula further including an open distal end, the resilient portion of the inner cannula being configured to protrude from the open distal end of the outer cannula when the inner cannula is fully inserted into the outer cannula.

Example 31

The biopsy system of Example 30, the resilient portion of the inner cannula being configured to protrude from the lateral aperture of the needle when the resilient portion is in the natural configuration.

Example 32

A method of deploying a biopsy marker, the method comprising: positioning an outer cannula into a first position relative to an inner cannula; and moving the inner cannula or the outer cannula to position the outer cannula in a second position relative to the inner cannula such that a resilient portion of the inner cannula protrudes from a distal end of the inner cannula to transition the resilient portion from a stressed straight position to a relaxed curved position; and actuating a push rod disposed within the inner cannula to deploy the biopsy marker from an open distal end of the inner cannula.

V. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A marker delivery device comprising:

(a) an outer cannula, the outer cannula defining a longitudinal axis and including an outer lumen, the outer lumen extending distally along the longitudinal axis from a handle to an open outer cannula distal end;

(b) an inner cannula assembly including an inner cannula and a grip, the inner cannula including a first inner cannula and a second inner cannula, the first inner cannula being removably coupled to the second inner cannula, the first inner cannula being disposed within the outer lumen and extending distally along the longitudinal axis from the grip to a first inner cannula open distal end, the second inner cannula having an open distal end and a resilient portion located proximate the open distal end and a straight portion located between the open distal end and the resilient portion, the straight portion and the resilient portion each including a closed tubular portion and having an outer diameter that is the same, the resilient portion being configured to move between a stressed configuration when engaged with the outer cannula and a relaxed configuration when disengaged with the outer cannula, the resilient portion being configured to be more parallel with the longitudinal axis when in the stressed configuration than the relaxed configuration, the resilient portion being configured to extend laterally from the outer cannula when in the relaxed configuration; and (c) a push rod, the push rod being disposed within an inner lumen of the inner cannula, the push rod being configured to deploy a marker through the open distal end.

2. The marker delivery device of claim 1, the push rod being configured to move within the inner lumen to deploy the marker through a needle.

3. The marker delivery device of claim 2, the needle having a closed distal end including a piercing tip, a distal portion of the needle being configured to translate a marker therethrough.

4. The marker delivery device of claim 1, the inner cannula being of a shape memory alloy.

5. The marker delivery device of claim 4, the shape memory alloy including nitinol or copper.

6. The marker delivery device of claim 5, the shape memory alloy including at least a one-way shape memory alloy.

7. The marker delivery device of claim 1, further comprising a plunger attached to the push rod, and a guard having a first position and a second position, the guard being configured to block access to the plunger in the first position, the guard being further configured to permit access to the plunger in the second position, the plunger being operable to deploy the marker when the guard is in the second position.

8. The marker delivery device of claim 7, the guard having a retaining feature including a detent or a locking pin.

9. The marker delivery device of claim 1, the push rod including a shape memory alloy.

10. The marker delivery device of claim 1, the push rod being rigid.

11. The marker delivery device of claim 1, the handle including a locking feature.

12. The marker delivery device of claim 11, the locking feature being configured to slidably couple the inner cannula within the outer cannula.

13. The marker delivery device of claim 11, the locking feature including a detent, a collet, or threads configured to engage a compressible member.

14. The marker delivery device of claim 1, the outer cannula being movably coupled to the inner cannula to translate the inner cannula between a plurality of positions.

15. The marker delivery device of claim 1, the second inner cannula including an attachment end and a deployment end, the resilient portion being between the attachment end and the deployment end.

16. A biopsy system configured to position a marker within soft tissue, comprising:

(a) a push rod;

(b) an inner cannula assembly including a grip and an inner cannula, the inner cannula extending distally along a longitudinal axis from the grip to an open distal end, the inner cannula having a resilient portion located proximate to the open distal end, the resilient portion defining a channel extending to the open distal end, the resilient portion having a natural configuration and a stressed configuration, the natural configuration corresponding to the resilient portion being deflected from the longitudinal axis, the stressed configuration corresponding to the resilient portion extending generally along the longitudinal axis, the channel being sized to translate the marker through the channel while in the stressed configuration, the push rod being configured to deploy the marker through the open distal end of the inner cannula and through the channel of the resilient portion;

(c) an outer cannula disposed entirely around the inner cannula and configured to transition the resilient portion of the inner cannula between the natural configuration and the stressed configuration; and (d) a needle configured to receive the inner cannula and the outer cannula, the needle including a side aperture, the resilient portion being configured to position the open distal end thereof proximate the side aperture when the inner cannula and outer cannula are fully inserted into the needle, the outer cannula including a length to thereby extend a portion of the outer cannula to the side aperture to thereby expose the portion of the outer cannula through the side aperture.

17. The biopsy system of claim 16, the outer cannula being configured to transition the resilient portion of the inner cannula from the stressed configuration to the natural configuration when the inner cannula is fully inserted into the outer cannula.

18. The biopsy system of claim 16, the outer cannula further including an open distal end, the resilient portion of the inner cannula being configured to protrude from the open distal end of the outer cannula when the inner cannula is fully inserted into the outer cannula.

19. The biopsy system of claim 16, the resilient portion of the inner cannula being configured to protrude from the side aperture of the needle when the resilient portion is in the natural configuration.

20. A method of deploying a biopsy marker into soft tissue, the method comprising:

positioning an outer cannula into a first position relative to an inner cannula; and moving the inner cannula or the outer cannula to position the outer cannula in a second position relative to the inner cannula such that a resilient portion and a straight portion of the inner cannula protrudes from a distal end of the outer cannula to transition the resilient portion from a stressed straight position to a relaxed curved position;

loading the biopsy marker into a proximal end of the inner cannula and then actuating a push rod disposed within the inner cannula to deploy the biopsy marker from an open distal end of the inner cannula;

advancing each of the outer cannula and the inner cannula into a needle having a lateral opening, and deploying the biopsy marker through the lateral opening of the needle to thereby position the biopsy marker lateral to each of the inner cannula, the outer cannula, and the needle and into the soft tissue.

* * * * *